United States Patent
Enhsen et al.

[11] Patent Number: 6,020,330
[45] Date of Patent: Feb. 1, 2000

[54] HYPOLIPIDEMIC 1,4-BENZOTHIAZEPINE-1, 1-DIOXIDES

[75] Inventors: Alfons Enhsen, Büttelborn; Eugen Falk, Frankfurt; Heiner Glombik, Hofheim; Siegfried Stengelin, Eppstein, all of Germany

[73] Assignee: Hoechst Aktiengesellschaft, Frankfurt am Main, Germany

[21] Appl. No.: 09/041,953

[22] Filed: Mar. 13, 1998

[30] Foreign Application Priority Data

Mar. 14, 1997 [EP] European Pat. Off. .............. 97104348

[51] Int. Cl.⁷ ..................... A61K 31/55; C07D 281/10; C07D 417/12
[52] U.S. Cl. ............................... 514/211; 540/552
[58] Field of Search ................ 540/552; 514/211

[56] References Cited

U.S. PATENT DOCUMENTS

| | | | |
|---|---|---|---|
| 5,580,866 | 12/1996 | Housley et al. | 514/211 |
| 5,663,165 | 9/1997 | Brieady | 514/211 |
| 5,723,458 | 3/1998 | Brieaddy et al. | 514/211 |

FOREIGN PATENT DOCUMENTS

| | | |
|---|---|---|
| WO 93/16055 | 8/1993 | WIPO . |
| WO 94/18183 | 8/1994 | WIPO . |
| WO 94/18184 | 8/1994 | WIPO . |
| WO 96/05188 | 2/1996 | WIPO . |

OTHER PUBLICATIONS

Grundy, "Cholesterol and Coronary Heart Disease", JAMA, vol. 256, No. 20, pp. 2849–2858, Nov. 28, 1986.
P. Tyle, Review, "Iontophoretic Devices for Drug Delivery", Pharmaceutical Research, vol. 3, No. 6, pp. 318–326, 1986.

*Primary Examiner*—Mukund J. Shah
*Assistant Examiner*—Ann M. Kessinger
*Attorney, Agent, or Firm*—Finnegan, Henderson, Farabow, Garrett & Dunner, L.L.P.

[57] ABSTRACT

The present invention is concerned with new hypolipidemic compounds, with processes and novel intermediates for their preparation, with pharmaceutical compositions containing them and with their use in medicine, particularly in the prophylaxis and treatment of hyperlipidemic conditions, such as atherosclerosis.

Compounds of the formula (I):

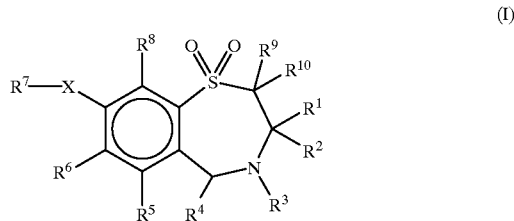

wherein $R^1$ to $R^{10}$ and X are a defined in the specification and are useful as hypolipidemic compounds.

18 Claims, No Drawings

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
　　　　(A) LENGTH: 30 base pairs
　　　　(B) TYPE: nucleic acid
　　　　(C) STRANDEDNESS: single
　　　　(D) TOPOLOGY: linear (ii) MOLECULE TYPE: DNA (genomic)

(xi) SEQUENCE DESCRIPTION: SEQ ID NO:1:

GTCAGACCAG AAGCTTGGGC TTCTGCAGAC                                   30

(2) INFORMATION FOR SEQ ID NO:2:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

ATCTTAATAA TATTCTAGAC AGTTTTTCTT TG                               32

(2) INFORMATION FOR SEQ ID NO:3:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

TAAAAGTTGG ATCCGGTAGA AGTAAACG                                    28

(2) INFORMATION FOR SEQ ID NO:4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

TCTGTTTTGT CCTCTAGATG TCTACTTTTC                                  30

(2) INFORMATION FOR SEQ ID NO:5:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

GGAGTGGTCT TCCACTGGAT CCCAGGAGGA TGGAGG                           36

(2) INFORMATION FOR SEQ ID NO:6:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

CCAGAATCCA GGCCACCTCT AGAAGGGCTA GGCTGT                           36

HYPOLIPIDEMIC 1,4-BENZOTHIAZEPINE-1,1-DIOXIDES

FIELD OF THE INVENTION

The present invention is concerned with new hypolipidemic compounds, with processes and novel intermediates for their preparation, with pharmaceutical compositions containing them and with their use in medicine, particularly in the prophylaxis and treatment of hyperlipidemic conditions, such as atherosclerosis.

BACKGROUND OF THE INVENTION

Hyperlipidemic conditions are often associated with elevated plasma concentrations of low density lipoprotein (LDL) cholesterol and very low density lipoprotein (VLDL) cholesterol. Such concentrations can be reduced by decreasing the absorption of bile acids from the intestine. One method by which this may be achieved is to inhibit the bile acid active uptake system in the terminal ileum. Such inhibition stimulates the conversion of cholesterol to bile acid by the liver and the resulting increase in demand for cholesterol produces a corresponding increase in the rate of clearance of LDL and VLDL cholesterol from the blood plasma or serum.

There has now been identified a novel class of heterocyclic compounds which reduce the plasma or serum concentrations of LDL and VLDL cholesterol and in consequence are particularly useful as hypolipidemic agents. By decreasing the concentrations of cholesterol and cholesterol ester in the plasma, the compounds of the present invention retard the build-up of atherosclerotic lesions and reduce the incidence of coronary heart disease-related events. The latter are defined as cardiac events associated with increased concentrations of cholesterol and cholesterol ester in the plasma or serum.

For the purposes of this specification, a hyperlipidemic condition is defined as any condition wherein the total cholesterol concentration (LDL+VLDL) in the plasma or serum is greater than 240 mg/dL (6.21 mmol/L) (J. Amer. Med. Assn., 256, 20, 2849– 2858 (1986)). International Patent Application No. WO 96/05188 describes compounds of formula (0)

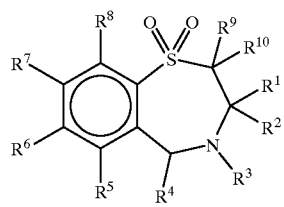

(0)

We have now discovered a group of compounds which have greater hypolipidemic activity in vivo than those specifically disclosed in International Patent Application No. WO 96105188. The compounds differ in the definition of group $R^7$. Accordingly, the present invention provides compounds of the formula (I):

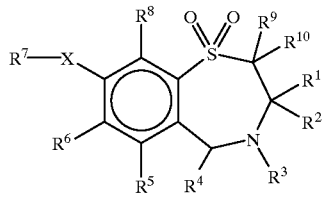

(I)

wherein
$R^1$ is a straight chained $C_{1-6}$ alkyl group;
$R^2$ is a straight chained $C_{1-6}$ alkyl group;
$R^3$ is hydrogen or a group $OR^{11}$ in which $R^{11}$ is hydrogen, optionally substituted $C_{1-6}$ alkyl or a $C_{1-6}$ alkylcarbonyl group;
$R^4$ is pyridyl or optionally substituted phenyl;
$R^5$, $R^6$ and $R^8$ are the same or different and each is selected from hydrogen, halogen, cyano, $R^{15}$-acetylide, $OR^{15}$, optionally substituted $C_{1-6}$ alkyl, $COR^{15}$, $CH(OH)R^{15}$, $S(O)_nR^{15}$, $P(O)(OR^{15})_2$, $OCOR^{15}$, $OCF_3$, $OCN$, $SCN$, $NHCN$, $CH_2OR^{15}$, $CHO$, $(CH_2)_pCN$, $CONR^{12}R^{13}$, $(CH_2)_pCO_2R^{15}$, $(CH_2)_pNR^{12}R^{13}$, $CO_2R^{15}$, $NHCOCF_3$, $NHSO_2R^{15}$, $OCH_2R^{15}$, $OCH=CHR^{15}$, $O(CH_2CH_2O)_nR^{15}$, $O(CH_2)_pSO_3R^{15}$, $O(CH_2)_pNR^{12}R^{13}$ and $O(CH_2)_pN^+R^{12}R^{13}R^{14}$ wherein
p is an integer from 1–4,
n is an integer from 0–3 and
$R^{12}$, $R^{13}$, $R^{14}$ and $R^{15}$ are independently selected from hydrogen and optionally substituted $C_{1-6}$ alkyl;
$R^7$ is a group of the formula

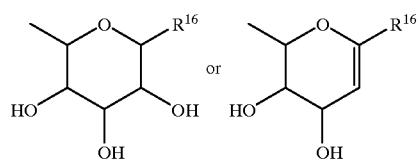

wherein the hydroxyl groups may be substituted by acetyl, benzyl, or

—$(C_1$–$C_6)$-alkyl-$R^{17}$ wherein the alkyl group may be substituted with one or more hydroxyl groups;
$R^{16}$ is —COOH, —$CH_2$—OH, —$CH_2$—O-Acetyl, —COOMe, —COOEt;
$R^{17}$ is H, —OH, —$NH_2$, —COOH or $COOR^{18}$;
$R^{18}$ is $(C_1$–$C_4)$-alkyl or —NH—$(C_1$–$C_4)$-alkyl;
X is —NH— or —O—; and
$R^9$ and $R^{10}$ are the same or different and each is hydrogen or $C_{1-6}$ alkyl;
and salts, solvates, and physiologically functional derivatives thereof.

When $R^4$ is a substituted phenyl group, there may be one to five, preferably one or two substituents which are the same or different and are each selected from halogen, hydroxy, nitro, phenyl-$C_{1-6}$ alkoxy, $C_{1-6}$ alkoxy, optionally substituted $C_{1-6}$ alkyl, $S(O)_nR^{15}$, $CO_2R^{15}$, $O(CH_2CH_2O)_nR^{15}$, $O(CH_2)_pSO_3R^{15}$, $O(CH_2)_pNR^{12}R^{13}$ and $O(CH_2)_pN^+R^{12}R^{13}R^{14}$ wherein $R^{12}$ to $R^{15}$, n and p are as hereinbefore defined.

Preferred embodiments of the compounds of formula (I) include compounds of the formula (III), (IV) or (IVa)

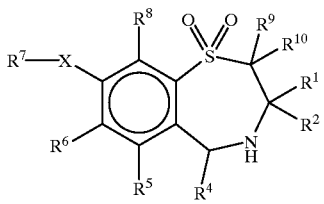
(III)

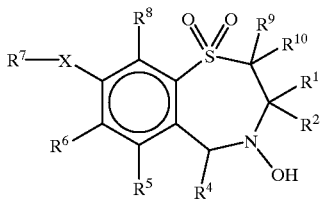
(IV)

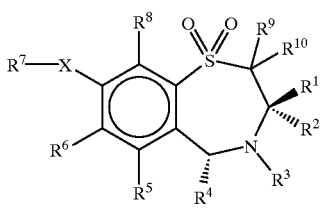
(IVa)

wherein $R^1$ to $R^{10}$ and X are as hereinbefore defined.

When one or more of $R^3$ to $R^6$, $R^8$ or $R^{11}$ to $R^{14}$ is a substituted $C_{1-6}$ alkyl group, or comprises a $C_{1-6}$ alkyl group the substituents may be the same or different and each is selected from hydroxy, halogen, $C_{1-6}$ alkyl, $C_{1-6}$ alkoxy, $COR^{20}$, nitrile, $CO_2R^{20}$, $SO_3R^{20}$, $NR^{21}R^{22}$, $N^+R^{21}R^{22}R^{23}$ wherein $R^{20}$ to $R^{23}$ are the same or different and each is selected from hydrogen or $C_{1-6}$ alkyl.

Suitably $R^1$ is methyl, ethyl or n-propyl and preferably $R^1$ is ethyl. Suitably $R^2$ is methyl, ethyl, n-propyl, n-butyl or n-pentyl. Preferably $R^2$ is n-butyl.

Preferably $R^5$ is hydrogen.

Suitably $R^7$ is selected from

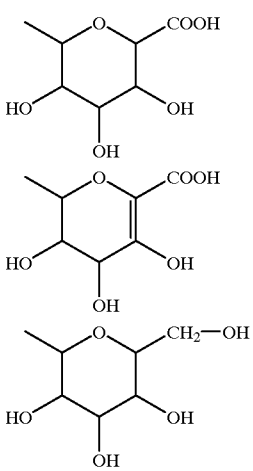

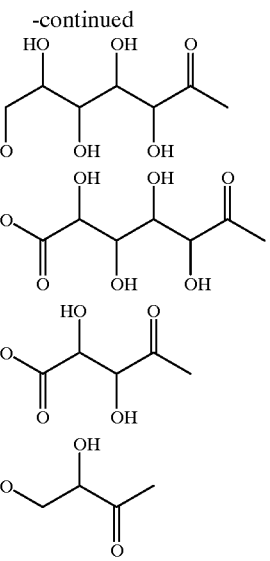

Suitably X is —O—.

Suitably $R^9$ and $R^{10}$ are hydrogen, methyl or ethyl, hydrogen. Preferably $R^9$ and $R^{10}$ are both hydrogen.

Suitably $R^4$ is pyridyl or phenyl optionally substituted, preferably at the 4- and/or 3-position by halogen, methyl, ethyl, methoxy, ethoxy, trifluoromethyl, hydroxy, carboxy or $O(CH_2)_3SO_3H$. Preferably $R^4$ is unsubstituted phenyl.

In the compounds of the formula (III): suitably at least one and preferably all of $R^5$, $R^6$ and $R^8$ are hydrogen. When $R^5$, $R^6$ and $R^8$ are other than hydrogen then they are suitably $C_{1-4}$ alkyl optionally substituted by fluorine, $C_{1-4}$ alkoxy, halogen or hydroxy, most suitably methyl, methoxy, hydroxy, trifluoromethyl or chloro and preferably methoxy.

In the compounds of the formula (IV): suitably two or three of $R^5$, $R^6$ and $R^8$ are hydrogen, the others being $C_{1-4}$ alkyl optionally substituted by fluoro, $C_{1-4}$ alkoxy, halogen or hydroxy and most suitably methyl, methoxy, hydroxy, trifluoromethyl or chloro and preferably methoxy.

In the compounds of formula (IVa): suitably at least one and preferably all of $R^5$, $R^6$ and $R^8$ are hydrogen. When $R^5$, $R^6$ and $R^8$ are other than hydrogen then they are suitably $C_{1-4}$ alkyl optionally substituted by fluorine, $C_{1-4}$ alkoxy, halogen or hydroxy, most suitably methyl, methoxy, hydroxy, trifluoromethyl or chloro and preferably methoxy. Most preferably, $R^1$ is n-butyl, $R^2$ is ethyl, $R^3$, $R^5$, $R^6$, $R^8$, $R^9$ and $R^{10}$ are hydrogen, $R^4$ is phenyl and $R^7$ is

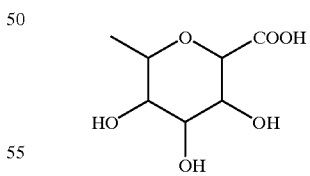

Pharmaceutically acceptable salts are particularly suitable for medical applications because of their greater aqueous solubility relative to the parent, ie basic, compounds. Such salts must clearly have a pharmaceutically acceptable anion or cation. Suitable pharmaceutically acceptable acid addition salts of the compounds of the present invention include those derived from inorganic acids, such as hydrochloric, hydrobromic, phosphoric, metaphosphoric, nitric, sulphonic and sulphuric acids, and organic acids, such as acetic, benzenesulphonic, benzoic, citric, ethanesulphonic, fumaric, gluconic, glycollic, isothionic, lactic, lactobionic, maleic, malic, methanesulphonic, succinic, p-toluenesulphonic, tartaric and trifluoroacetic acids. The chloride salt is particularly preferred for medical purposes. Suitable pharmaceutically acceptable base salts include ammonium salts, alkali metal salts, such as sodium and potassium salts, and alkaline earth salts, such as magnesium and calcium salts.

Salts having a non-pharmaceutically acceptable anion are within the scope of the invention as useful intermediates for the preparation or purification of pharmaceutically acceptable salts and/or for use in non-therapeutic, for example, in vitro, applications.

The term "physiologically functional derivative" as used herein refers to any physiologically acceptable derivative of a compound of the present invention, for example, an ester, which upon administration to a mammal, such as a human, is capable of providing (directly or indirectly) such a compound or an active metabolite thereof.

A further aspect of the present invention is prodrugs of the compounds of the invention. Such prodrugs can be metabolised in vivo to give a compound according to the invention. These prodrugs may or may not be active in their own right.

The compounds of the present invention can also exist in different polymorphic forms, for example, amorphous and crystalline polymorphic forms. All polymorphic forms of the compounds of the present invention are within the scope of the invention and are a further aspect thereof.

The term "alkyl" as used herein refers, unless otherwise stated, to a monovalent straight or branched chain radical. Likewise, the term "alkoxy" refers to a monovalent straight or branched chain radical attached to the parent molecular moiety through an oxygen atom. The term "phenylalkoxy" refers to a monovalent phenyl group attached to a divalent $C_{1-6}$ alkylene group which is itself attached to the parent molecular moiety through an oxygen atom.

The compounds of formula (I) exist in forms wherein the carbon centres —C($R^1$)($R^2$)— and —CHR$^4$— is/are chiral. The present invention includes within its scope each possible optical isomer substantially free, i.e. as associated with less than 5%, of any other optical isomer(s), and mixtures of one or more optical isomers in any proportions, including racemic mixtures.

For the purposes of this specification, the absolute chiralities of the aforementioned carbon centres are given in the order —C($R^1$)($R^2$), then —CHR$^4$—.

In those cases where the absolute stereochemistry at —C($R^1$)($R^2$)— and —CHR$^4$— has not been determined, the compounds of the invention are defined in terms of the relative positions of the $R^1/R^2$ and H/$R^4$ substituents. Thus those compounds wherein the bulkier of the $R^1$ and $R^2$ substituents, i.e. the substituent of higher mass, and the $R^4$ substituent are both located on the same side of the thiazepine ring are referred to herein as "cis", and those compounds in which the bulkier of the $R^1$ and $R^2$ substituents are located on opposite sides of the ring are referred to as "trans" and are preferred. It will be evident to a skilled person that both "cis" and "trans" compounds of the invention can each exist in two enantiomeric forms which are individually designated "(+)-" or "(−)-" according to the direction of rotation of a plane of polarised light when passed through a sample of the compound. Cis or trans compounds of the invention in which the individual anantiomers have not been resolved are referred to herein using the prefix "(+)-".

According to further aspects of the invention, there are also provided:

(a) compounds of formula (I) and pharmaceutically acceptable salts, solvates and physiologically functional derivatives thereof for use as therapeutic agents, particularly in the prophylaxis and treatment of clinical conditions for which a bile acid uptake inhibitor is indicated, for example, a hyperlipidemic condition, such as atherosclerosis;

(b) pharmaceutical compositions comprising a compound of formula (I) or one of its pharmaceutically acceptable salts, solvates, or physiologically functional derivatives, at least one pharmaceutically acceptable carrier and, optionally, one or more other physiologically active agents;

(c) the use of a compound of formula (I) or of a pharmaceutically acceptable salt, solvate, or physiologically functional derivative thereof in the manufacture of a medicament for the prophylaxis or treatment of a clinical condition for which a bile acid uptake inhibitor is indicated, for example, a hyperlipidemic condition, such as atherosclerosis;

(d) a method of inhibiting the absorption of bile acids from the intestine of a mammal, such as a human, which comprises administering an effective bile acid absorption inhibiting amount of a compound of formula (I) or of a pharmaceutically acceptable salt, solvate, or physiologically functional derivative thereof to the mammal;

(e) a method of reducing the blood plasma or serum concentrations of LDL and VLDL cholesterol in a mammal, such as a human, which comprises administering an effective cholesterol reducing amount of a compound of formula (I) or of a pharmaceutically acceptable salt, solvate, or physiologically functional derivative thereof to the mammal;

(f) a method of reducing the concentrations of cholesterol and cholesterol ester in the blood plasma or serum of a mammal such as a human, which comprises administering an effective cholesterol and cholesterol ester reducing amount of a compound of formula (I) or of a pharmaceutically acceptable salt, solvate, or physiologically functional derivative thereof to the mammal;

(g) a method of increasing the fecal excretion of bile acids in a mammal, such as a human, which comprises administering an effective bile acid fecal excretion increasing amount of a compound of formula (I) or of a pharmaceutically acceptable salt, solvate, or physiologically functional derivative thereof to the mammal;

(h) a method for the prophylaxis or treatment of a clinical condition in a mammal, such as a human, for which a bile acid uptake inhibitor is indicated, for example, a hyperlipidemic condition, such as atherosclerosis, which comprises administering a therapeutically effective amount of a compound of the formula (I) or of a pharmaceutically acceptable salt, solvate, or physiologically functional derivative thereof to the mammal;

(i) a method of reducing the incidence of coronary heart disease-related events in a mammal, such as a human, which comprises administering an effective coronary heart disease-related events reducing amount of a compound of formula (I) or of a pharmaceutically acceptable salt, solvate, or physiologically functional derivative thereof;

(j) a method of reducing the concentration of cholesterol in the blood plasma or serum of a mammal, such as a human, which comprises administering an effective cholesterol reducing amount of a compound of formula (I);

(k) processes for the preparation of compounds of formula (I) (including salts, solvates and physiologically functional derivatives thereof as defined herein); and (l) novel chemical intermediates in the preparation of compounds of formula (I).

(m) the compounds of Synthetic Example 1 to 5 as hereinafter disclosed.

Hereinafter all references to "compound(s) of formula (I)" refer to compound(s) of formula (I) as described above together with their salts, solvates and physiologically functional derivatives as defined herein.

The amount of a compound of formula (I) which is required to achieve the desired biological effect will, of course, depend on a number of factors, for example, the specific compound chosen, the use for which it is intended, the mode of administration and the clinical condition of the recipient. In general, a daily dose is the range of from 0.3 mg to 100 mg (typically from 3 mg to 50 mg) per day per kilogram bodyweight, for example, 3–10 mg/kg/day. An intravenous dose can, for example, be in the range of from 0.3 mg to 1.0 mg/kg, which can conveniently be administered as an infusion of from 10 ng to 100 ng per kilogram per minute. Infusion fluids suitable for this purpose can contain, for example, from 0.1 ng to 10 mg, typically from 1 ng to 10 mg, per millilitre. Unit doses can contain, for example, from 1 mg to 10 g of the active compound. Thus ampoules for injection can contain, for example, from 1 mg to 100 mg and orally administrable unit dose formulations, such as tablets or capsules, may contain, for example, from 1.0 to 1000 mg, typically from 10 to 600 mg. In the case of pharmaceutically acceptable salts, the weights indicated above refer to the weight of the benzothiazepine ion derived from the salt.

For the prophylaxis or treatment of the conditions referred to above, the compounds of formula (I) can be used as the compound per se, but are preferably presented with an acceptable carrier in the form of a pharmaceutical composition. The carrier must, of course, be acceptable in the sense of being compatible with the other ingredients of the composition and must not be deleterious to the recipient. The carrier can be a solid or a liquid, or both, and is preferably formulated with the compound as a unit-dose composition, for example, a tablet, which can contain from 0.05% to 95% by weight of the active compound. Other pharmacologically active substances can also be present including other compounds of formula (I). The pharmaceutical compositions of the invention can be prepared by any of the well known techniques of pharmacy consisting essentially of admixing the components.

Pharmaceutical compositions according to the present invention include those suitable for oral, rectal, topical, buccal (e.g. sub-lingual) and parenteral (e.g. subcutaneous, intramuscular, intradermal, or intravenous) administration, although the most suitable route in any given case will depend on the nature and severity of the condition being treated and on the nature of the particular compound of formula (I) which is being used. Enteric-coated and enteric-coated controlled release formulations are also within the scope of the invention. Preferred are acid and gastric juice resistant formulations. Suitable enteric coatings include cellulose acetate phthalate, polyvinylacetate phthalate, hydroxypropylmethylcellulose phthalate and anionic polymers of methacrylic acid and methacrylic acid methyl ester.

Pharmaceutical compositions suitable for oral administration can be presented in discrete units, such as capsules, cachets, lozenges, or tablets, each containing a predetermined amount of a compound of formula (I); as a powder or granules; as a solution or a suspension in an aqueous or non-aqueous liquid; or as an oil-in-water or water-in-oil emulsion. As indicated, such compositions can be prepared by any suitable method of pharmacy which includes the step of bringing into association the active compound and the carrier (which can constitute one or more accessory ingredients). In general, the compositions are prepared by uniformly and intimately admixing the active compound with a liquid or finely divided solid carrier, or both, and then, if necessary, shaping the product. For example, a tablet can be prepared by compressing or moulding a powder or granules of the compound, optionally with one or more accessory ingredients. Compressed tablets can be prepared by compressing, in a suitable machine, the compound in a free-flowing form, such as a powder or granules optionally mixed with a binder, lubricant, inert diluent and/or surface active/dispersing agent(s). Moulded tablets can be made by moulding, in a suitable machine, the powdered compound moistened with an inert liquid diluent.

Pharmaceutical compositions suitable for buccal (sublingual) administration include lozenges comprising a compound of formula (I) in a flavored base, usually sucrose and, acacia or tragacanth, and pastilles comprising the compound in an inert base such as gelatin and glycerin or sucrose and acacia.

Pharmaceutical compositions suitable for parenteral administration conveniently comprise sterile aqueous preparations of a compound of formula (I), preferably isotonic with the blood of the intended recipient. These preparations are preferably administered intravenously, although administration can also be effected by means of subcutaneous, intramuscular, or intradermal injection. Such preparations can conveniently be prepared by admixing the compound with water and rendering the resulting solution sterile and isotonic with the blood. Injectable compositions according to the invention will generally contain from 0.1 to 5% w/w of the active compound.

Pharmaceutical compositions suitable for rectal administration are preferably presented as unit-dose suppositories. These can be prepared by admixing a compound of formula (I) with one or more conventional solid carriers, for example, cocoa butter, and then shaping the resulting mixture.

Pharmaceutical compositions suitable for topical application to the skin preferably take the form of an ointment, cream, lotion, paste, get spray, aerosol, or oil. Carriers which can be used include vaseline, lanoline, polyethylene glycols, alcohols, and combinations of two or more thereof. The active compound is generally present at a concentration of from 0.1 to 15% w/w of the composition, for example, from 0.5 to 2%.

Transdermal administration is also possible. Pharmaceutical compositions suitable for transdermal administration can be presented as discrete patches adapted to remain in intimate contact with the epidermis of the recipient for a prolonged period of time. Such patches suitably contain the active compound in an optionally buffered, aqueous solution, dissolved and/or dispersed in an adhesive, or dispersed in a polymer. A suitable concentration of the active compound is about 1% to 35%, preferably about 3% to 15%. As one particular possibility, the active compound can be delivered from the patch by electrotransport or iontophoresis, for example, as described in Pharmaceutical Research, 2(6), 318 (1986).

The compounds of the invention can be prepared by conventional methods known to a skilled person or in an analogous manner to processes described in the art.

For example, compounds of the formula (I) can be prepared by a process which comprises a) acylation of a compound of fomula (II)

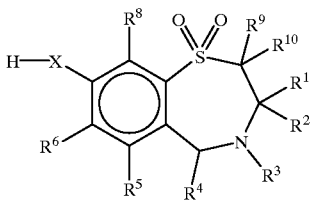

(II)

by standard procedures (e.g. with N,N-carbonyl-diimidazole) at the —X—H group or
   a) alkylation of a compound of fomula (II) by standard procedures at the —X—H group or
   a) glycosylation or glucuronidation a compound of fomula (II) at the —X—H group, especially using the imidate method and
   b) cleavage of protecting groups, especially of hydroxyl and amino functional groups, e.g. acetyl by hydrolysis, benzyl by hydrogenolysis.

The compounds of formula (II) can be prepared according to the method of preparation disclosed in WO 96/05188.

The compounds of formula (I) substantially free, of other optical isomers can be obtained either by chiral synthesis, for example, by the use of the appropriate chiral starting material(s), such as the aziridine, or by resolution of the products obtained from achiral syntheses, for example, by chiral hplc or by classical resolution with chiral acids.

Optional conversion of a compound of formula (I), or a compound of formula (I) comprising a basic substituent, to a corresponding acid addition salt may be effected by reaction with a solution of the appropriate acid, for example, one of those recited earlier. Optional conversion of a compound of formula (I) comprising an acidic substituent to a corresponding base salt may be effected by reaction with a solution of the appropriate base, for example, sodium hydroxide. Optional conversion to a physiologically functional derivative, such as an ester, can be carried out by methods known to those skilled in the art or obtainable from the chemical literature.

In addition, compounds of the formula (I) may be converted to different compounds of the formula (I) by standard methods known or available from the literature to those skilled in the art, for example by alkylation of a hydroxy group.

Comparison of the hypolipidemic activity of of the compounds according to the invention with compound no. 11 of WO 96/05188:

In order to prove the greater hypolipidemic activity of the compounds according to the invention tests were carried out by means of three genetically modified cell lines. These were derivatives of the generally known "Chinese hamster ovary" (CHO) cell line, which on account of incorporated expression plasmids additionally produced sodium-dependent bile acid transporters. The first cell line (CHO/pRIBAT8) was in this case the ileal transporter of the rabbit (RIBAT), the second (CHO/pHIBAT8) the ileal transporter of the human (HIBAT) and the third (CHO/pHLBAT5) the hepatic transporter of the human. All plasmids were based on the standard plasmid pCDNA1neo, which as important elements has a cytomegaloviral promoter for the permanent expression of heterologous genes and a gene for the production of cell resistance against the substance G418.

The starting material for the production of the plasmid for the RIBAT-producing cell line (pRIBAT8) was total RNA of the terminal ileum of the rabbit. From this by means of an RT-PCR procedure (reverse transcriptase reaction, followed by a polymerase chain reaction) with the aid of the oligonucleotides 5'-gtcagaccagaagcttgggcttctgcagac-3'(SEQ ID NO:1) and 5'-atcttaataatattctagacagtttttctttg-3'(SEQ ID NO:2), a cDNA was synthesized which contained the total protein-coding region of the RIBAT, and also 41 base pairs on the 5'-adjacent and 31 base pairs on the 3'-adjacent untranslated region. This region was flanked by cleavage sites for the restriction enzymes Hind3 (at the 5'-end) and Xba1 (at the 3'-end). The obtained cDNA and DNA of plasmid pcDNA1 neo were digested using the two restriction enzymes mentioned and resulting fragments were combined by means of ligase to give the expression plasmid pRIBAT8.

The plasmid for the HIBAT-producing cell line (pHIBAT8) was prepared analogously to pRIBAT8. In this case, total RNA of human terminal ileum and the oligonucleotides 5'-taaaagttggatccggtagaagtaaacg-3'(SEQ ID NO:3) and 5'-tctgttttgtcctctagatgtctacttttc-3'(SEQ ID NO:4) served as starting material. Besides the total protein-coding region of HIBAT, the resulting cDNA also contained 97 base pairs on the 5'-adjacent and 5 base pairs on the 3'-adjacent untranslated region. This region was flanked by cleavage sites for the restriction enzymes BamH1 (at the 5'-end) and Xba1 (at the 3'-end). The obtained cDNA and DNA of plasmid pcDNA1 neo were digested using the two restriction enzymes mentioned and resulting fragments were combined by means of ligase to give the expression plasmid pRIBAT8.

A commercially available cDNA gene bank prepared from human liver served as starting material for the plasmid for the preparation of the HLBAT-producing cell line (pHLBAT5). From this by means of a PCR procedure (polymerase chain reaction) with the aid of the oligonucleotides 5'-ggagtggtcttccactggatcccaggaggatggagg-3'(SEQ ID NO:5) and 5'-ccagaatccaggccacctctagaagggctaggctgt-3' (SEQ ID NO:6), a cDNA was synthesized which contained the total protein-coding region of the HLBAT, and also 7 base pairs on the 5'-adjacent and 6 base pairs on the 3'-adjacent untranslated region. This region was flanked by cleavage sites for the restriction enzymes BamH1 (at the 5'-end) and Xba1 (at the 3'-end). The obtained cDNA and DNA of plasmid pcDNA1neo were digested using the two restriction enzymes mentioned and resulting fragments were combined by means of ligase to give the expression plasmid pHLBAT5.

For the preparation of the genetically modified cell lines, CHO cells were transfected with DNA from pRIBAT8, pHIBAT8 or pHLBAT5 and cells which developed resistance against the selection substance G418 were selectively additionally cultured by addition of the substance to the cell medium. The cells CHO/pRIBAT8, CHO/pHIBAT8 and CHO/pHLBAT5 were then isolated from the amount of G418-resistant cells and pure clonal lines were cultured therefrom. The tool used for following the isolation process was in this case a fluorescent bile acid derivative (3β-NBD-NCT; N-[7-(4-nitrobenzo-2-oxa-1,3-diazol)]-3β-amino-7a, 12a-dihydroxy-5β-cholan-24-oyl)-2'-aminoethanesulfonate. Cells with intact bile acid transporters rapidly absorbed this substance from the cell medium and as a result became fluorescent. They could thereby be easily differentiated from cells without intact bile acid transporters with the aid of a fluorescence microscope.

All three cell lines transported radiolabelled taurocholic acid efficiently from the extracellular medium into the cell interior. This process was sodium-dependent. In contrast to this, CHO cells without intact bile acid transporters only absorbed very small amounts of taurocholic acid. Building on this knowledge, a characterization of test substances according to the invention was carried out as follows: cells of the type CHO/pRIBAT8, CHO/pHIBAT8 or CHO/pHLBAT5 were simultaneously exposed in culture dishes to radiolabelled taurocholic acid and a test substance and the absorption of radioactive material by the cells was measured. The test substance concentrations here were varied systematically from dish to dish and all other parameters were kept constant. To prepare them for experiment, the cells were routinely cultured in medium (minimum essential medium (MEM); 1% MEM non-essential amino acid solution; 10% foetal calf serum; 400 g/ml of G418) in culture flasks, if required removed from their environment by means of trypsin, inoculated in diluted form into culture dishes (diameter: 3.5 cm) and additionally cultured in medium. Shortly before reaching cell confluence, the medium was removed from the cells and the contents of each dish were washed with 2 times 1.5 ml of PBS (Dulbecco's phosphate-buffered saline solution). After removing the wash solution, 1 ml of a defined concentration of test substance in PBS was added to each dish and they were incubated at 21° C. for 30 minutes. This preincubation solution was then replaced by a test solution which contained [24-$^{14}$C]- taurocholic acid in a concentration of 4.3 M and of a specific radioactivity of 7400 Bq/ml, but otherwise had the same volume and the same composition as the pre-incubation solution. The cells were exposed to the test solution at 21° C. for 30 minutes and then washed with 5 times 1.5 ml of PBS per dish. To lyse the cells, 1 ml of an aqueous solution containing 0.1 mol/l of NaOH and 0.1% (weight/volume) of SDS was added to each dish, which was incubated for 30 minutes at 21° C. and triturated. Finally, the contents of each dish were mixed with 10 ml of a commercially available scintillator solution and the radioactivity taken up by the cells was determined with the aid of a scintillation-measuring apparatus.

To assess the transport results, the radioactivity values were not plotted directly, but their % relationship to a control value in the case of which measurement had been carried out without inhibiting test substance. Half-maximal inhibition values ($IC_{50}$) resulted from this graphically or arithmetically:

| | | |
|---|---|---|
| Example 3 | $IC_{50}$ (RIBAT) | : 70 nm = 0,07 µM |
| Example 11 of WO 96/05188 | $IC_{50}$ (RIBAT) | : 4µM |

An analogous investigation of the effect of the same substances on the transport of the cell line CHO/pHIBAT8 showed that here the corresponding $IC_{50}$ value varied approximately within the same order of magnitude. In contrast to this, the $IC_{50}$ value determined with the cell line CHO/pHLBAT5 was several powers of ten higher. This shows that compounds according to the invention can exert a comparable effect on orthologous sodium-dependent bile acid transporters of various species and, in contrast to this, the effect on paralogous transporters of other organs can be very much smaller.

For a better understanding of the invention, the following Example is given by way of illustration and is (e.g. with N,N-carbonyl-diimidazole) not to be construed in any way as limiting the scope of the invention.

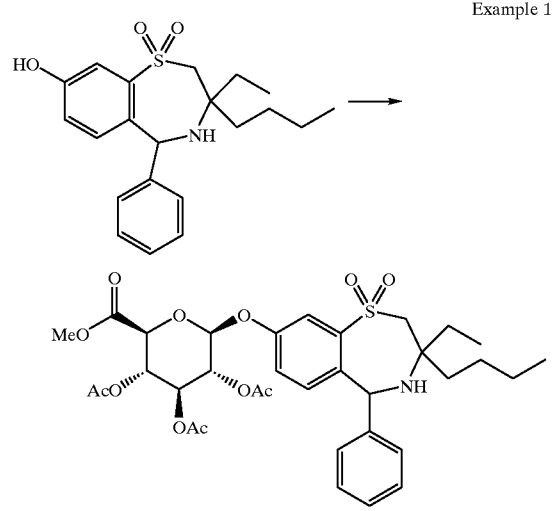

Example 1

To a solution of 2.9 g methyl-2,3,4-tri-O-acetyl-glucuronate in 100 ml dry dichloromethane at room temperature under Argon is added 4.6 ml trichloroacetonitrile and the solution was stirred for 10 min. Then 730 mg potassium carbonate is added. After 30 min of stirring at room temperature the mixture is filtered through a short pat of silica, eluting with ether. The filtrate is concentrated in vacuo to yield the crude product as a pale yellow solid (3.7 g). 1.0 g of this product were dissolved in 15 ml dry dichloromethane and added to a solution of Phenol I (trans racemate) in 30 ml dry dichloromethane. After cooling to −10° C. 0.32 ml BF$_3$·OEt$_2$ were added and after 30 min at −10° C. the mixture was stired for 20 h at room temperature. Then the reaction was diluted with dichloromethane and washed with aqueous sodium bicarbonate and brine. The combined organic phases were dried over Na$_2$SO$_4$ and evaporated in vacuo. The crude product was purified by silica gel chromatography (n-heptane/ethyl acetate, 2:1) to obtain 625 mg of Example 1. $R_f$=0.17 (n-heptane/ethyl acetate 1:1).

$C_{34}H_{43}NO_{12}S$ (689): MS (FAB, 3-NBA): 690 (M+H+)

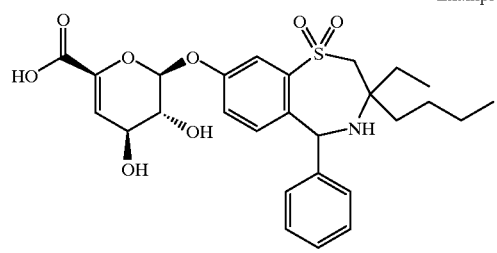

Example 2

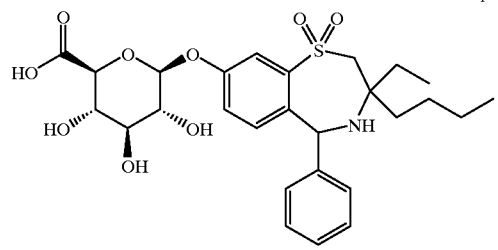

Example 3

To a solution of 900 mg Example 1 in 45 ml methanol were added 15 ml of 1N NaOH. After 4 h at room temperature 150 ml $H_2O$ were added and the organic solvent evaporated in vacuo. The aqueous solution was adjusted to pH 3 with 2N HCl and evaporated to dryness. Chromatography over siliva gel ($CH_2Cl_2$/MeOH/33% aq. $NH_3$, 30:10:3) yielded two fractions.

1. Fraction: Example 2, $R_f$=0.85 ($CH_2Cl_2$/MeOH/33% aq. $NH_3$, 30:10:3) ($C_{27}H_{33}NO_8S$ (531): MS (ESI): 532 (M+H+)
2. Fraction: Example 3, $R_f$=0.52 ($CH_2Cl_2$/MeOH/33% aq. $NH_3$, 30:10:3) ($C_{27}H_{35}NO_9S$ (549): MS (FAB, 3-NBA): 550 (M+H+)

Example 4

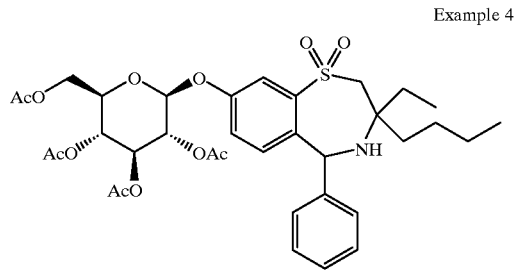

Example 4 was obtained in analogy to example 1
$R_f$=0.20 (n-heptane/ethyl acetate 1:1 )
$C_{35}H_{45}NO_{12}S$ (703): MS (ESI): 704 (M+H+)

Example 5

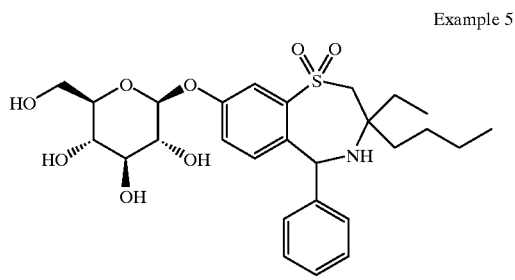

Example 5 was obtained in analogy to example 2
$R_f$=0.20 ($CH_2Cl_2$/MeOH33% aq. $NH_3$, 60:10:3)

$C_{27}H_{37}NO_8S$ (535): MS (FAB, 3-NBA): 536 (M+H+)
NMR-data of Example 3

| | Chemical Shifts in $MeOH_{d4}$ at 300 K | | | |
|---|---|---|---|---|
| Position | Isomer A $1_H$ | Isomer B $1_H$ | Isomer A $13_C$ | Isomer B $13_C$ |
| 1 | — | — | 58.51 | 58.51 |
| 2 | 3.50/3.14 | 3.50/3.16 | 64.63 | 64.63 |
| 3 | — | — | 142.36 | 142.36 |
| 4 | — | — | 140.61 | 140.61 |
| 5 | 6.00 | 6.01 | 55.74 | 55.74 |
| 6 | 1.57/1.44 | 1.57/1.44 | 34.38 | 34.38 |
| 7 | 0.88 | 0.88 | 7.94 | 7.94 |
| 8 | 2.22/1.79 | 2.22/1.79 | 31.95 | 31.95 |
| 9 | 1.17 | 1.17 | 26.22 | 26.22 |
| 10 | 1.26 | 1.26 | 24.06 | 24.06 |
| 11 | 0.81 | 0.81 | 14.31 | 14.31 |
| 12 | — | — | 143.98 | 143.98 |
| 13 | 7.39 | 7.39 | 129.05 | 129.05 |
| 14 | 7.38 | 7.38 | 129.36 | 129.36 |
| 15 | 7.29 | 7.29 | 128.09 | 128.09 |
| 16 | 6.61 | 6.61 | 131.10 | 131.10 |
| 17 | 7.17 | 7.17 | 121.72 | 121.72 |
| 18 | — | — | 157.69 | 157.69 |
| 19 | 7.72 | 7.73 | 117.81 | 117.81 |
| 20 | 4.91 | 4.91 | 102.46 | 102.46 |
| 21 | 3.48 | 3.48 | 74.62 | 74.62 |
| 22 | 3.48 | 3.48 | 77.71 | 77.71 |
| 23 | 3.50 | 3.50 | 73.53 | 73.53 |
| 24 | 3.70 | 3.70 | 76.45 | 76.45 |
| 25 | — | — | 176.21 | 176.21 |

We claim:

1. A compound of formula (I)

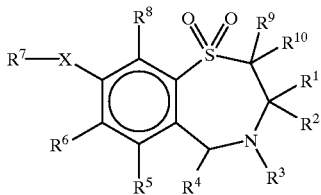

(I)

wherein $R^1$ is a straight chain $C_{1-6}$ alkyl group;

$R^2$ is a straight chain $C_{1-6}$ alkyl group;

$R^3$ is hydrogen or a group $OR^{11}$ in which $R^{11}$ is hydrogen, optionally substituted $C_{1-6}$ alkyl or a $C_{1-6}$ alkylcarbonyl group;

$R^4$ is pyridyl or an optionally substituted phenyl;

$R^5$, $R^6$ and $R^8$ are the same or different and each is selected from:

hydrogen, halogen, cyano, $R^{15}$-acetylide, $OR^{15}$, optionally substituted $C_{1-6}$ alkyl, $COR^{15}$, $CH(OH)R^{15}$, $S(O)_nR^{15}$, $P(O)(OR^{15})_2$, $OCOR^{15}$, $OCF_3$, $OCN$, $SCN$, $NHCN$, $CH_2OR^{15}$, $CHO$, $(CH_2)_pCN$, $CONR^{12}R^{13}$, $(CH_2)_pCO_2R^{15}$, $(CH_2)_pNR^{12}R^{13}$, $CO_2R^{15}$, $NHCOCF_3$, $NHSO_2R^{15}$, $OCH_2OR^{15}$, $OCH=CHR^{15}$, $O(CH_2CH_2O)_nR^{15}$, $O(CH_2)_pSO_3R^{15}$, $O(CH_2)_pNR^{12}R^{13}$ and $O(CH_2)_pN^+R^{12}R^{13}R^{14}$ wherein p is an integer from 1–4, n is an integer from 0–3 and $R^{12}$, $R^{13}$, $R^{14}$ and $R^{15}$ are independently selected from hydrogen and optionally substituted $C_{1-6}$ alkyl;

$R^7$ is a group of the formula

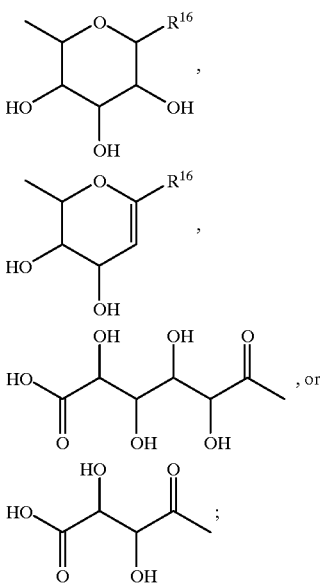

wherein the hydroxyl groups may be substituted by acetyl, benzyl, or $—(C_1–C_6)$-alkyl-$R^{17}$, wherein the alkyl group may be substituted with one or more hydroxyl groups;

$R^{16}$ is —COOH, —$CH_2$—OH, —$CH_2$—O-Acetyl, —COOMe or —COOEt;

$R^{17}$ is H, —OH, —$NH_2$, —COOH or $COOR^{18}$;

$R^{18}$ is $(C_1–C_4)$-alkyl or —NH—$(C_1–C_4)$-alkyl;

X is —NH— or —O—; and $R^9$ and $R^{10}$ are the same or different and each is hydrogen or $C_{1-6}$ alkyl; and salts thereof.

2. A compound of claim 1, represented by formula (III):

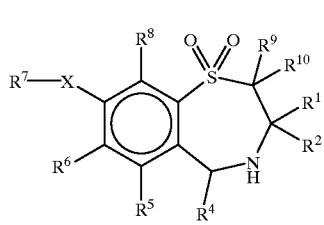

(III)

wherein $R^1$ to $R^{10}$ and X are as defined in claim 1 or a salt thereof. acceptable carrier.

3. A compound of claim 1, represented by formula (IV):

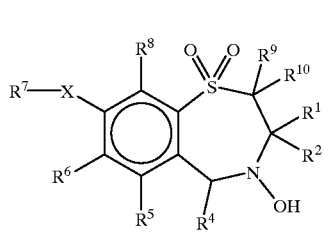

(IV)

wherein $R^1$ to $R^{10}$ and X are as defined in claim 1 or a salt thereof.

4. A compound of claim 1, represented by formula (IVa):

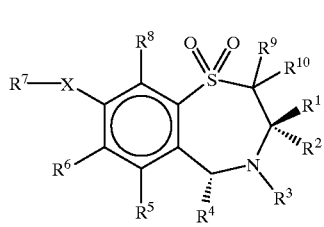

(IVa)

wherein $R^1$ to $R^{10}$ and X are as defined in claim 1 or a salt thereof.

5. A compound of claim 1, wherein X is —O— and $R^7$ is selected from:

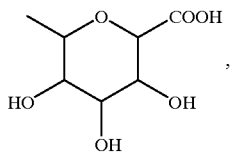

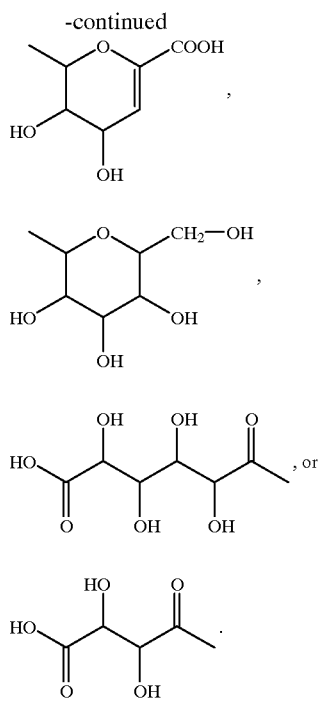

6. A compound of formula (II):

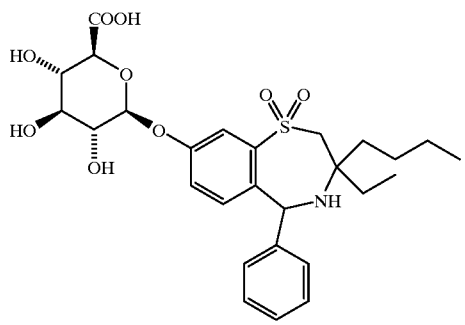

or a salt thereof.

7. A pharmaceutical composition, comprising a compound of claim 1 or a salt thereof, together with a suitable pharmaceutically acceptable carrier.

8. An acid and gastric juice resistant pharmaceutical composition, comprising a compound of claim 1 or a pharmaceutically acceptable salt thereof, together with a suitable pharmaceutically acceptable enteric coating.

9. A method of inhibiting bile acid uptake in a mammal comprising administering to a mammal in need thereof an effective amount of a compound of claim 1, or a pharmaceutically acceptable salt thereof.

10. A method of treating or preventing hyperlipidemia in a mammal, comprising administering to a mammal in need thereof an effective amount of a compound of claim 1 or a pharmaceutically acceptable salt thereof.

11. A method of claim 10, wherein the hyperlipidemia is atherosclerosis.

12. A pharmaceutical composition, comprising a compound of claim 6 or a salt thereof, together with a suitable pharmaceutically acceptable carrier.

13. An acid and gastric juice resistant pharmaceutical composition, comprising a compound of claim 6 or a pharmaceutically acceptable salt thereof, together with a suitable pharmaceutically acceptable enteric coating.

14. A method of inhibiting bile acid uptake in a mammal comprising administering to a mammal in need thereof an effective amount of a compound of claim 6 or a pharmaceutically acceptable salt thereof.

15. A method of treating or preventing hyperlipidemia in a mammal, comprising administering to a mammal in need thereof an effective amount of a compound of claim 6 or a pharmaceutically acceptable salt thereof.

16. A method of claim 13, wherein the hyperlipidemia is atherosclerosis.

17. A method of preparing a compound of claim 1, including a salt thereof, comprising a) acylation of a compound of formula (II)

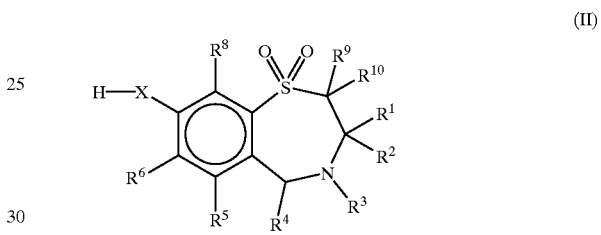

(II)

by standard procedures at the —X—H group or a) alkylation of the compound of formula (II) by standard procedures at the —X—H group or a) glycosylation or glucuronidation of the compound of formula (II) at the —X—H group, and b) cleavage of protecting groups.

18. A method of preparing a compound of claim 6, including a salt thereof, comprising a) acylation of a compound of formula (II)

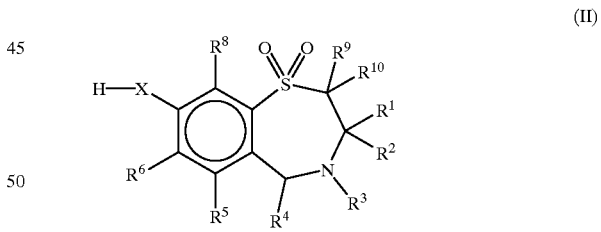

(II)

by standard procedures at the —X—H group or a) alkylation of the compound of formula (II) by standard procedures at the —X—H group or a) glycosylation or glucuronidation of the compound of formula (II) at the —X—H group, and b) cleavage of protecting groups.

* * * * *

UNITED STATES PATENT AND TRADEMARK OFFICE
CERTIFICATE OF CORRECTION

PATENT NO.: 6,020,330

DATED: February 1, 2000

INVENTORS: Alfons ENHSEN et al.

It is certified that an error appears in the above-identified patent and that said Letters Patent is hereby corrected as shown below:

On the Title Page, Item [57], in the Abstract, line 9, "a defined" should read --as defined--.

Claim 2, Column 18, line 28, after "thereof.", delete "acceptable carrier.".

Claim 16, Column 20, line 16, "claim 13" should read --claim 15--.

Signed and Sealed this

First Day of May, 2001

Attest:

NICHOLAS P. GODICI

Attesting Officer

Acting Director of the United States Patent and Trademark Office